United States Patent [19]

Silver et al.

[11] 4,275,729

[45] Jun. 30, 1981

[54] ADJUSTABLE DOSAGE SYRINGE

[75] Inventors: Jules Silver, P.O. Box 1188, Norwich, Conn. 06360; James F. Ennis, Preston, Conn.

[73] Assignee: Jules Silver, Norwich, Conn.

[21] Appl. No.: 88,936

[22] Filed: Oct. 29, 1979

[51] Int. Cl.³ .............................................. A61M 5/00
[52] U.S. Cl. .......................... 128/218 C; 128/218 PA
[58] Field of Search ........... 128/218 C, 218 R, 218 P, 128/218 PA, 234, 215, 216, 213

[56] References Cited

U.S. PATENT DOCUMENTS 3,563,240  2/1971  Silver .................................... 128/234

FOREIGN PATENT DOCUMENTS 804455  4/1951  Fed. Rep. of Germany ....... 128/218 C
370878  2/1907  France ................................. 128/218 C
1577954  10/1969  France ................................. 128/218 C

*Primary Examiner*—John D. Yasko
*Attorney, Agent, or Firm*—Murray and Whisenhunt

[57] ABSTRACT

An adjustable dosage syringe is provided wherein the syringe plunger has sets of multiple closely spaced indentations along the length of the plunger, and a dosage selection ring disposed around the plunger. The inside circumference of the dosage selection ring has protuberances which are registerable with and receivable in one of the indentations of the sets of indentations so that when one protuberance is received in an indentation of the first set of indentations, the other protuberance is also received in an indentation in the second set of indentations. Channels are disposed along the length of the plunger for simultaneously and slidably receiving the protuberances so that the ring is longitudinally slidable along the length of the plunger. Thus, any desired dosage may be achieved by rotating the ring so that the protuberances are disposed in the channel, sliding the ring along the length of the plunger, to that point corresponding to the desired dosage, and rotating the ring so that the protuberances are received by the indentations. The plunger is then forced into the syringe until the ring is engaged by the barrel of the syringe and stops further movement of the plunger into the syringe.

10 Claims, 4 Drawing Figures

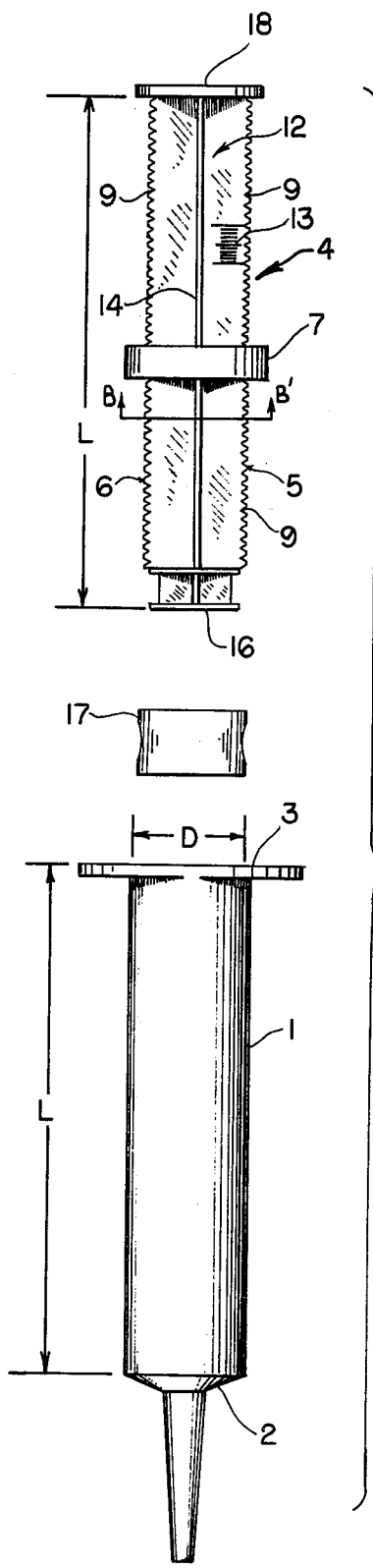
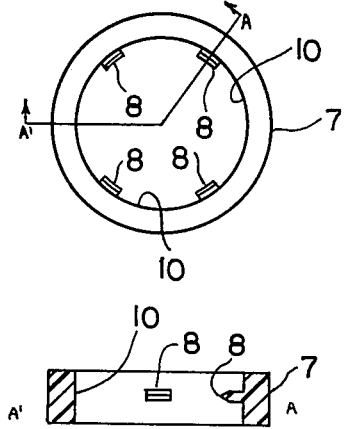
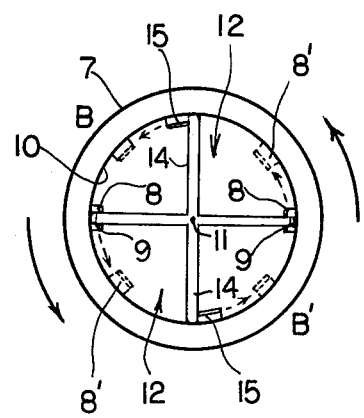
Fig. 1
Fig. 2
Fig. 3
Fig. 4

ADJUSTABLE DOSAGE SYRINGE

The present invention relates to an adjustable dosage syringe and more particularly to such a syringe where multiple doses can be expelled from a single loading of the syringe and wherein the increment of variability of dosage is exceedingly small. Even more particularly, the present invention relates to such syringes wherein the desired dosage can be rapidly set on the syringe.

BACKGROUND OF THE INVENTION

Adjustable dosage syringes have been used in the art for either adjusting the dosage for a particular administration of the contents of the syringe and/or for delivering multiple dosages of the contents of the syringe in multiple separate injections. For example, in veterinary use, the dosage of a particular drug administered to an animal may vary considerably with the weight of an animal. Thus, when a herd of livestock is to be injected with a drug, the careful and sterile loading of a syringe in the field is not always practical, and it is conventional in the art to provide the veterinarian with a syringe capable of adjustment of the dosage delivered from that syringe in injecting individual animals. These syringes are normally disposable syringes and, accordingly, the veterinarian can select the proper dose for an individual animal, rapidly set the syringe for delivering only that dose, inject the animal, and dispose of the syringe with the remaining drug content therein. Alternatively, when a drug is to be administered to a large number of animals, multiple doses for a number of animals may be contained in a single syringe and the veterinarian can select the proper dosage for each animal, rapidly set that dosage on the syringe and serially inject the animals with the proper dosage.

Since a large number of animals are often treated in a short period of time, it is most important that the adjustable syringe be capable of rapid adjustment for dosage delivered and be accurate in the dosage. Further, since these syringes are normally disposable, it is imperative that the syringes be of such construction that they are inexpensive to manufacture. Further, since it is conventional in the art that the syringe and drug be supplied as a total package from the manufacturer, the adjustable syringe must be capable of delivering dosages of varying amounts, consistent with the weight of the animal, and that the increment of dosage with which the syringe may be set is relatively small.

A number of syringes of this nature have been made available to the art. Thus, U.S. Pat. No. 3,563,240 provides a syringe with a plunger having peripheral thread thereon, and a cooperating threaded nut. By threading the nut up and down of the syringe plunger, adjustable dosage of the drug contained in the syringe may be delivering by way of the nut limiting the depression of the plunger into the syringe barrel. However, manually threading the nut up and down the plunger is relatively time-consuming, particularly when the dosage requirement from animal to animal varies considerably and the threading of the nut must be accurately performed in order to ensure that the correct dosage is given. Manufacture of such a syringe is also expensive, since it requires manual manipulation to thread the nut on the plunger during the assembling process.

Efforts have been made in the art to overcome such disadvantages, notable among which is the known "split-ring" syringe wherein the "nut" is releasably hinged about the circumference thereof. Whereby, the nut can be opened, manually slid to the portion of the plunger desired for the appropriate dose, closed on the threads, and the appropriate dose discharged from the syringe. However, here again, this requires manual opening and closing of the hinged "nut" and can be time-consuming for the reasons expressed above.

Older approaches in the art avoided some of the problems discussed above by providing a plunger with various types of replaceable stop means, e.g. pins, clips and the like, but these approaches were too cumbersome for field use. Another approach in the older art was that of providing indentations in a ring disposed about the plunger whereby the indentations would allow the ring to be lifted and moved along the plunger to discrete recesses in the legs of the plunger wherein the ring could be dropped into and set the dosage discharged by the plunger. U.S. Pat. No. 2,856,925 is representative thereof. This older approach in the art, while being relatively rapid to operate, suffered from the disadvantages that the dosage was fixed by the size of the recesses in the legs of the plunger, and the necessary clearance in the recesses for allowing the ring to drop thereinto could not accurately set the dosage discharged from the syringe.

Accordingly, while the advances in the art have improved the accuracy of the dosage which can be delivered, i.e. by virtue of the threaded nut arrangement and the like, these advances have been accompanied by less convenient and rapid use of the syringes. It would therefore be of considerable advantage in the art to provide an adjustable dose syringe which can not only be rapidly changed to set the dosage delivered but can very accurately set that dosage and provide for very small increments of dosage adjustment.

OBJECTS OF THE INVENTION

Therefore, it is an object of the invention to provide an adjustable dose syringe wherein the desired dosage can be set within very small increments of dosage. It is a further object of the invention to provide such a syringe where the dosage adjustment can be rapidly set. It is a further object of the invention to provide such a syringe wherein the dosage delivered can be very accurate. Finally, it is an object of the invention to provide such an adjustable dosage syringe wherein multiple doses can be delivered from a single syringe, and each dosage can be rapidly and accurately set and the increment of dosage adjustment is quite small. Other objects will be apparent from the following description of the invention and claims.

BRIEF DESCRIPTION OF THE DRAWINGS

FIG. 1 is an exploded view of the syringe of the present invention, showing a preferred embodiment thereof.

FIG. 2 is a top view of the ring associated with the plunger of the syringe of the present invention, showing a preferred embodiment thereof.

FIG. 3 is a cross-sectional view along A—A' of FIG. 2.

FIG. 4 is a cross-sectional view of the plunger with ring thereon along line B—B' of FIG. 1.

BRIEF DESCRIPTION OF THE INVENTION

The invention is based on several primary considerations. Firstly, in order to provide the necessary accuracy of dosage delivered from the syringe, slots as used in the older prior art approaches, discussed above, may not be used, since dosage variability associated therewith is too great. To achieve the desired accuracy of dosage, positive stop means associated with the plunger of an adjustable dose syringe must be of the fineness and accuracy of the threads of the prior art approach. Secondly, detachable stop means, such as clips, pins, and the like, are too cumbersome and apt to be lost, and cannot be used in commercially acceptable adjustable dosage syringes. Thirdly, relatively tedious manipulations of the adjustment mechanism, such as threading a nut, are too time-consuming for field use.

Based on these three considerations, it has been discovered that the objects of the invention can be fulfilled by providing multiple closely spaced indentations on the plunger, somewhat in the nature of threads, but wherein the dosage selection ring can be rapidly moved up and down the plunger, without threading or the like, by virtue of channels in the plunger receiving protuberances on the inside circumference of the dosage selection ring. Dosage adjustment is achieved by engaging those protuberances in the indentations by rotation of the ring, and hence, the protuberances, out of the channels and into the indentations.

Thus, broadly stated, the present invention is an improvement in an adjustable syringe having a syringe barrel with an internal length and diameter which forms a volume sufficient to contain multiple dosages of a liquid, a discharge end at one end of the barrel length, a plunger receiving end at the opposite end of the barrel length, and a plunger slidably disposed within the barrel and having a length greater than the length of the barrel. The present improvement comprises a plunger having at least first and second sets of multiple closely spaced indentations disposed along the length thereof. A dosage selection ring is disposed around the plunger and is rotatable about its longitudinal axis. At the base one pair of protuberances is disposed on the inside circumference of the ring. Each of the protuberances is in a configuration suitable for being in register with and received in one indentation of the respective first and second sets of indentations. Accordingly, when one of the protuberances is received in the first set of indentations, the other protuberance is received on the second set of indentations. At least two channels are disposed along the length of the plunger for simultaneously slidably receiving, respectively, the protuberances, so that the ring is longitudinally slidable along the length of the plunger. Thus, any desired dosage may be set by rotating the ring so that the protuberances are received in the channels, sliding the ring along the length of the plunger to that point thereof corresponding to the desired dosage, rotating the ring so that the protuberances are received in the indentation, and sliding the plunger into the barrel of the syringe until the ring is engaged by the plunger receiving end of the barrel. Thus, the desired dosage is positively expelled out of the discharge end of the syringe.

Preferably, the indentations are so closely spaced that the dosage of liquid expelled can be varied by as little as 10% of the volume of the syringe, usually as little as 5%, and optimally as little as 2%.

DETAILED DESCRIPTION OF THE INVENTION

The invention can best be understood by reference to the drawings. FIG. 1 shows an exploded view of a preferred embodiment of the present invention. Thus, the syringe is composed of a barrel 1 having an internal length L and an internal diameter D. The volume formed by the dimensions L and D are sufficient to contain multiple dosages of a liquid, e.g. drug, disposed in the syringe. The barrel has a discharge end 2, and a plunger receiving end 3, at the opposite end of the barrel length. A plunger, generally 4, has a length L greater than the length of the barrel, for reasons explained more fully hereinafter. The plunger has at least first and second sets of multiple closely spaced indentations 5 and 6 disposed along the length thereof. A dosage selection ring 7 is disposed around the plunger and is rotatable about the longitudinal axis thereof.

As can be seen in FIG. 2, the dosage selection ring 7 has protuberances 8 (four protuberances being shown) which are of a configuration suitable for being in register with and received in an individual indentation 9 disposed on plunger 4. A suitable cross-section of a protuberance is shown in FIG. 3 which is a cross-section along A—A' of FIG. 2. As can be seen from FIGS. 2 and 3, the protuberances are disposed on the inside circumference 10 of dosage selection ring 7. The protuberances are disposed on the inside circumference of the ring so that when one of the protuberances is received in the first set of indentations 5, the other protuberance is received in the second set of indentations 6.

As can be seen in FIG. 4, the protuberances 8 are brought into register with indentations 9 by rotation of the dosage selection ring 7 about axis 11 of plunger 4. In this embodiment, full engagement or disengagement may be achieved with only one quarter turn (or 90° rotation) of the dosage selection ring 7.

In order to adjust the dosage, there are at least two channels 12 disposed along the length of plunger 4. These channels will simultaneously and slidably receive, respectively, the protuberances 8 so that the ring is longitudinally slidable along the length of the plunger. Hence, ring 7, as shown in FIG. 4, is simply rotated counterclockwise, which disengages protuberances 8 from indentations 9 and places the protuberances in channels 12 as shown by the phantom outline of protuberances 8'. When the protuberances 8' are in channel 12, the ring 7 may be rapidly moved up and down plunger 4 to set the dosage as required. While not required, the plunger 4 may have disposed along its length indices 13 which correspond to the position of the ring on the plunger for expelling the volume indicated by the indices. Once ring 7 has been placed at the desired volume to be expelled, protuberances 8' are brought into register with indentations 9, as shown by protuberances 8 in FIG. 4. Protuberances 8 are thereby received in indentations 9 of both the first and second sets of indentations.

Accordingly, any desired dosage may be set by rotating the ring 7 so that the protuberances are received in channels 12, sliding the ring along the length of the plunger 4 to that point corresponding to the desired dosage, rotating the ring 7, e.g. ¼ turn, so that protuberances 8 are received in indentations 9 and then sliding plunger 4 into barrel 1 until the ring 7 is engaged by the plunger receiving end 3 of barrel 1. Thus, the desired dosage of liquid is expelled out of discharge end 2 of the barrel.

In order to achive the objects of the invention, indentations 9 are so closely spaced that the dosage of liquid expelled from the barrel can be varied by as little as 10% of the total volume of the syringe. However, usually, the indentations are so closely spaced that the dosage expelled can be varied as little as 5% and more usually as little as 2%. Thus, for example, in this latter regard, there must be 50 indentations in each set of indentations along the length of plunger 4.

While the drawings show only two sets of indentations, 5 and 6, there may be at least three or even four sets of indentations, or more. The increased number of sets of indentations continues to improve the rigidity of the ring 7 when pressed against end 3 of barrel 1 and increases the accuracy of delivery of dosage from the barrel. It will be appreciated, however, that there must be a corresponding number of channels 12. Thus, with three or four sets of indentations, there must be correspondingly, three or four sets of channels, and, of course three or four corresponding protuberances.

When ring 7 is rotated so that protuberances 8 are engaged in indentations 9, that engagement should be sufficient that a positive, but releaseable lock is provided. This lock can be simply by frictional engagement, but if desired, conventional ball and socket engagement or like mechanical releaseable locks may be used.

Also, if desired, as shown in FIG. 4, the indentations and protuberances may be so configured that the protuberances are receivable in the indentations by rotation of the ring in only either one of clockwise or counterclockwise rotation, and respective channels are disposed, correspondingly, in either the clockwise or counterclockwise directions. Thus, it will be seen that ribs 14 of FIG. 4 (and FIG. 1) have no indentations therein. Ring 7, nevertheless, has blind protuberances 15 disposed on the inside circumference 10 such that they will contact ribs 14 when protuberances 8 are in register with and received by indentations 9. Thus, in rotating ring 7, a positive stop of that rotation is achieved when indentations 9 and protuberances 8 are engaged and received therein. This is convenient for rapid operation of the syringe, since no care must be taken to ensure that the protuberances 8 are engaged with and received by indentations 9.

It will also be appreciated from the foregoing that protuberances 8 are receivable in indentations 9 only by rotation of the ring 7 in the clockwise direction and that release of the ring 7 can be achieved only by rotation thereof in the counterclockwise direction. This is also convenient for rapid field use. This, of course, also necessitates, that the channels are disposed, correspondingly, in either the clockwise or counterclockwise directions, in reference to the protuberances. In the example shown in FIG. 4, channels 12 are disposed counterclockwise from the protuberances, when the protuberances are engaged in indentations 9.

Of course, other positive stop means, rather than blind protuberances 15 may be used. Thus, the indentations may be tapered so that protuberances 8 may be engaged in the indentations from only one side thereof, thus producing the counterclockwise/clockwise relationship.

Conveniently, the syringe is manufactured in conventional injection molding techniques of plastics material, although glass, metal and other materials may be used if desired. The syringe can be inexpensively manufactured by the arrangement shown in FIG. 1, whereby ring 7 is simply slidable onto plunger 4 from seal end 16 of plunger 4. After the ring has been slid onto the plunger 4, seal 17 is pushed onto seal end 16 to complete the plunger. Alternatively, thumb pad 18 may be removable, by means well known in the art, for slipping ring 7 onto the plunger 4, e.g., with a monolithic plastic seal.

The specific shape of indentations 9 are not narrowly critical. Thus, as shown in FIG. 1, they may have a configuration of threads. However, the cross-sectional configuration may be square, rectangular, oval and the like, and this only necessitates that protuberances 8 have a similar configuration, in order that the required engagement therebetween may be achieved.

Typically, syringes of the present nature will have total volumes of as little as 3 cc's up to 100 cc's, but volumes between 20 and 50 cc's are more usual. A multiple dose syringe of approximately 30 cc's has been found to be particularly useful, since it may be used for administering a drug of usual dosages of 1 to 5 cc's to a number of animals. In a 30 cc syringe, of the overall configuration shown in FIG. 1, it is only necessary to have 30 indentations in each set of indentations in order to achieve a dosage increment of 1 cc or a dosage increment of 3.3%. With only 60 indentations, a dosage increment of 0.5 cc or approximately 1.5% may be achieved, and with only 100 indentations, a dosage increment of 3/10 cc may be achieved or a dosage increment of 1%. When the volume indices are marked for each indentation, ring 7 can be set for any dosage volume rapidly and with extreme accuracy, simply by rotating ring 7, sliding it to the desired dosage and rotating the ring back into engagement between the protuberances and indentations. The dosage thus set is both extremely accurate in volume, can be set to very fine dosage increments, and dosage adjustments can be very rapidly achieved. Thus, all of the objects of the invention have been achieved by the present arrangement.

The syringe may be filled by conventional automatic filling machines. The present syringe has a further advantage in this regard. During handling of the plunger in filling machines, the selector ring must be placed on the plunger near the thumb pad end prior to filling and at the zero point (the end of the plunger opposite the thumb pad) after filling. With the present syringe, this may be done instantly, by sliding back and forth, as opposed to the prior devices which required tedious threading of the selector ring back and forth.

While the invention has been described in reference to the preferred embodiments of the invention, modifications thereof will be quite apparent to those skilled in the art, and it is intended that the invention embrace those apparent modifications. Thus, the invention extends to the spirit and scope of the annexed claims.

What is claimed is:

1. In an adjustable dosage syringe having a syringe barrel with an internal length and diameter which forms a volume sufficient to contain multiple dosages of a liquid, a discharge end at one end of the barrel length, a plunger receiving end at the opposite end of the barrel length, and a plunger slidably disposed within the barrel and having a length greater than the length of the barrel, the improvement comprising a plunger having at least first and second sets of multiple closely spaced indentations disposed along the length thereof, a dosage selection ring disposed around the plunger and rotatable about the longitudinal axis thereof, at least one pair of protuberances each of which is of a configuration suitable for being in register with and received in one indentation of the respective first and second sets of indentations and said protuberances being disposed on the inside circumference of said ring so that when one of the protuberances is received in the first set of indentations, the other protuberance is received in the second set of indentations, at least two channels disposed along the length of the plunger for simultaneously slidably receiving, respectively, the said protuberances so that the said ring is longitudinally slidable along the length of the plunger, whereby any desired dosage may be set by rotating the ring so that the protuberances are received in said channels, sliding the ring along the length of the plunger to that part thereof corresponding to the desired dosage, rotating the ring so that the protuberances are received by the indentations and sliding the plunger into the barrel until the ring is engaged by the said plunger receiving end of the barrel and the desired dosage of liquid is expelled out of the discharge end of the barrel.

2. The syringe of claim 1 wherein the indentations are so closely spaced that the dosage of liquid expelled can be varied by as little as 10% of the volume of the syringe.

3. The syringe of claim 1 wherein the indentations are so closely spaced that the dosage of liquid expelled can be varied by as little as 5% of the volume of the syringe.

4. The syringe of claim 1 wherein the indentations are so closely spaced that the dosage of liquid expelled can be varied by as little as 2% of the volume of the syringe.

5. The syringe of claim 1 wherein there are at least three sets of indentations and at least three corresponding channels and protuberances.

6. The syringe of claim 1 wherein there are at least four sets of indentations and at least four corresponding channels and protuberances.

7. The syringe of claim 1 wherein the indentations and protuberances are so configured so that the protuberances are receivable in the indentations by rotation of the ring in only either one of clockwise or counterclockwise rotation and the respective channels are disposed, correspondingly, in either the clockwise or counterclockwise directions.

8. The syringe of claim 7 wherein there is engagement between the protuberances and the indentations sufficient that a positive but releasable lock is provided.

9. The syringe of claim 8 wherein the lock is frictional engagement.

10. The syringe of claim 1 wherein indicies of dispelled volumes are disposed along the length of the plunger which correspond to the position of the said ring on the plunger.

* * * * *